US00PP07788P

United States Patent [19]

Drewlow

[11] Patent Number: Plant 7,788

[45] Date of Patent: Feb. 11, 1992

[54] IMPATIENS PLANT NAMED AMBROSIA

[75] Inventor: Lyndon W. Drewlow, Ashtabula, Ohio

[73] Assignee: Mikkelsens, Inc., Ashtabula, Ohio

[21] Appl. No.: 607,022

[22] Filed: Oct. 31, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner

[57] ABSTRACT

A new and distinct cultivar of Impatiens plant named Ambrosia, characterized by its deep orange-red flower color, approximately 5.5 cm flower diameter, solid dark green leaves with purplish cast and scabrous upper surface, usually two flower buds per axil, reddish-purple smooth stems, and its reddish spur on mature flower bud.

1 Drawing Sheet

The present invention comprises a new and distinctive cultivar of Impatiens plant, botanically known as Impatiens, and known by the cultivar name Ambrosia. The new cultivar was developed by me through controlled breeding by crossing the cultivar Aurore (seed parent) with the male or pollen parent identified as Mikkelsen Seedling No. 87-683-6. Aurore is disclosed in U.S. Plant Pat. No. 6,685.

Asexual reproduction by terminal or stem cuttings has shown that the unique features of this new Impatiens are stabilized and are produced true to type in successive propagations.

The following combination of characteristics distinguish Ambrosia from both its parent varieties and other cultivated Impatiens of this type known and used in the floriculture industry, including the comparison cultivars referred to, namely, Nova (U.S. Plant Pat. No. 6,004); Aurore (U.S. Plant Pat. No. 6,685), and Eclipse (U.S. Plant Pat. No. 4,689). Color references are to the Royal Horticultural Society Colour Chart (R.H.S.).

1. Ambrosia has deep orange-red flowers (34A) which are slightly deeper in color than the flowers of Nova and Aurore (both of which are 33A to B), and much deeper than the flower color of Eclipse (43B).

2. Ambrosia has a flower diameter of approximately 5.5 cm, larger than Aurore (5.0 cm), and similar to Eclipse and Nova.

3. Flower pedicels of Ambrosia are yellow-green, while Nova, Aurore and Eclipse have reddish-purple pedicels.

4. Ambrosia has a scabrous upper leaf surface while Nova has a hirsute upper leaf surface, and Aurore and Eclipse have glabrous upper leaf surfaces.

5. Ambrosia, Nova, and Eclipse have similar sized leaves at 12 to 13 cm long and 3.0 to 3.5 cm wide, with Aurore having a shorter (11 to 12 cm) and broader (3.5 to 4 cm) leaf.

6. Ambrosia and Eclipse have solid dark green leaves with a purplish cast, while Nova and Aurore have dark green leaves with cream variegation around the midrib, especially under high light conditions.

7. Ambrosia is 7 to 10 days earlier to bloom than Eclipse, and similar in blooming period to Nova and Aurore.

8. Ambrosia usually has two flower buds per leaf axil, usually being similar in this respect to Aurore and Nova. Eclipse normally has only one flower per leaf axil.

9. Ambrosia and Eclipse have reddish-purple, smooth stems, while Nova has a hirsute stem of the same color, and Aurore has a lighter reddish stem that is smooth.

10. Ambrosia and Eclipse have a 5 cm long reddish spur on a mature flower bud with a green tip, while Nova has a 4.0 cm long spur that is completely reddish in color, and Aurore has a 4.0 cm reddish spur with a green tip.

The accompanying colorerd photograph illustrates the overall appearance of this cultivar taken as a face view of the plant and showing the colors as true as reasonably possible to obtain in a colored reproduction of this type. The photo was taken on Dec. 20, 1989 under natural light on an overcast day under double poly greenhouse covering at Ashtabula, Ohio.

The following is a detailed description of my new cultivar, based on plants produced in greenhouses in Ashtabula, Ohio during the summer season of the year. Plants were grown in 15 cm pots and measurements were taken 16 weeks after rooted cuttings were planted. Height measurements were taken from the soil line of the container. The plants were grown as 65°-68° F. night temperatures, under 3500 to 4500 foot candles of light, and with 240 ppm nitrogen, 240 ppm potassium, and 175 ppm phosphorous nutritional levels with trace elements added. Habit of growth, foliage coloration, leaf variegation, size of leaves and flower size will be greatly influenced by nutritional and environmental conditions. Color references are made to the Royal Horticultural Society Colour Chart (R.H.S.) except where general terms of ordinary dictionary significance are used.

Parentage: A controlled cross between female parent Aurore and male parent Mikkelsen Seedling No. 87-683-6.

Propagation:

A. *Type cutting.*—Stem 15 mm long will develop to 4 to 5 cm long in 18 to 21 days.

B. *Time to initiate roots.*—8-10 days at 23° C. summer: 10-123 days at 20° C. winter.

C. *Rooting habit.*—Heavy, fibrous.

Plant Description: Habit of growth, foliage coloration and size of leaf will be greatly influenced by nutritional and environmental conditions. Thus, data that follows was taken from plants grown under the conditions stated above.

A. *Form and habit of growth.*—Semi-upright to mounded, highly self-branched; semi-tall in height; continuous flowerng; flowering both inside and over the top of leaf canopy; vigorous growing, flowering herb.

B. *Foliage description.*—Dark green with purple cast and reddish-purple midrib; petiole and under side of leaf solid dark green with no variegation. 1Size: Mature leaf is 12 to 13 cm long and 3.0 to 3.5 cm wide. 2Shape: Lanceolate with acuminate apex. 3Texture: Upper scarbrous; lower glabrous. 4. Margin: Slightly serrate wth fine ciliate. 5. Color: Young foliage with top side, 147A; under side 178A. Mature foliage top side 147A; under side 178A. 6. Venation: Pinnate with a reddish cast.

Flowering Description:

A. *Flowering habits.*—Flowers continuously from leaf whorl in a progressively orderly manner with usually two flowers per leaf axil. All first flowers in a whorl open before the second flower in the leaf axil of that whorl. When second flowers of a leaf axial start to open, the first flower of a leaf axil of whorl above start to open. It takes 5 to 7 days for a mature bud to fully open and then the flower may last two weeks or longer depending on the environment.

B. *Natural flowering season.*—Indeterminant and continuous. Quantity of flowering increases with increasing levels of light.

C. *Flower buds.*—Ellipsoidal, flowers prefect; prange-red spur up to 5.0 cm long with green tip on a mature bud with the throat behind the ovary and originating from the major sepal.

D. *Flowers borne.*—Individual green pedicels from a whorl of 4 to 5 leaves, flowering progressively around the whorl as buds and leaves develop. Most leaf axils have two flowers.

E. *Quantity of flowers.*—Very floriferous because of hightly self-branching nature of plant; long lasting flowers and the presence of two flowers at each leaf axil results in flowers which are open at three leaf whorls at one time.

F. *Diameter of flower.*—5.0 to 5.5 cm.

G. *Petals.*—1. Shaped: Heart-shape; standard is largest petal. 2. Color: Top side when opening 34A, fading to 34B; under side 34B-C. 3. Number of petals: Five. 4. Size of petals: Standard — 3.3 cm wide by 2.5 cm long; two equal shallow cut lobes. Wings. — 2.8 cm wide by 2.5 cm long; two unequal lobes, moderate cut. Keel — 3.0 cm wide by 2.7 cm long; two unequal lobes, moderate cut.

H. *Reproductive Organs.*—1. Stamens: five in number; anther shape is hooded; color reddish-purple. Pollen color is cream. 2. Pistils: Stigma shape is five segmented column; reddish color. Style color is reddish. Ovaries, five in number; 6 mm mature size; reddish color.

Disease resistance: No significant disease and insect problems to date, and scabrous upper leaf surface may discourage red spider mite infestation.

Other Important Characteristics 1. Early flowering and excellent self-branching nature allowing cultivar to be grown in a 10 cm pot but it is also vigorous so that it can be grown in 15 to 15 cm containers.

2Has shown the ability to tolerate both high temperatures and sun light and continue to flower, as well as cool temperatures (40°-50° F.) Thus, growing season can be expanded.

3. Ambrosia is semi-upright in growth habit, similar in height to the more upright growing Aurore, not as tall as Eclipse, but taller than the compact and mounded Nova.

4. Ambrosia is highly self-branched as is Nova and Aurore, with all three having a dense growth habit. Eclipse, however, has an open, less branched growth habit.

I claim:

1. A new and distinct cultivar of Impatiens plant named Ambrosia, as illustrated and described.

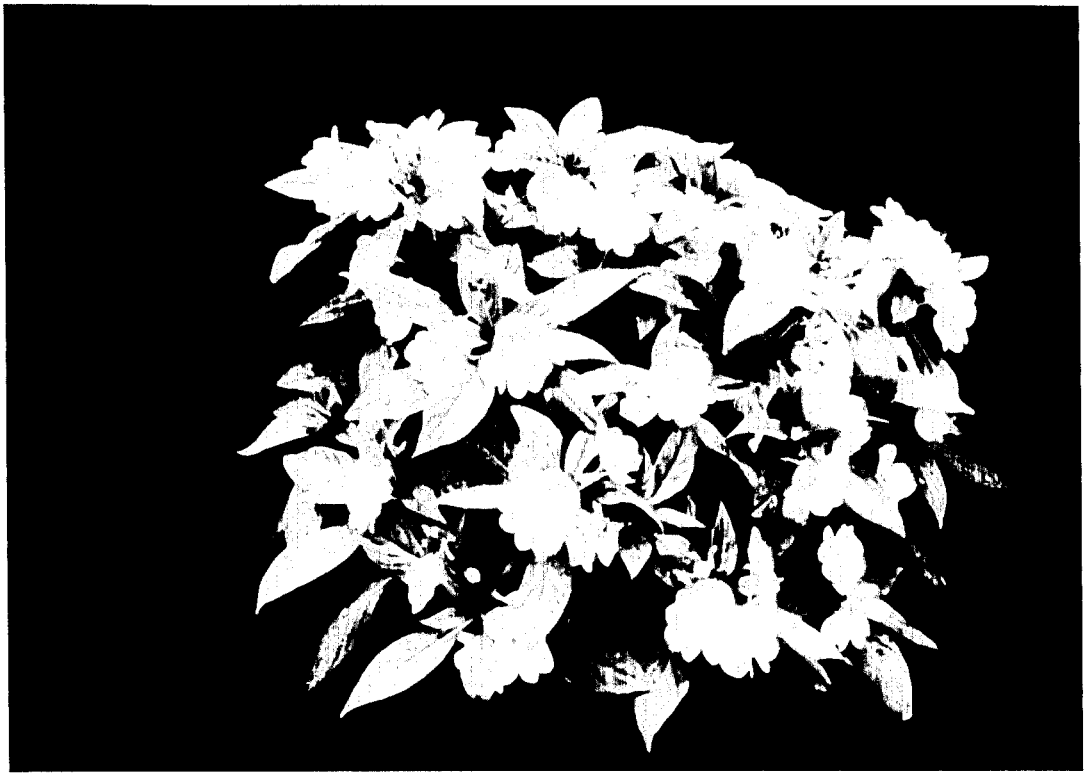

* * * * *